United States Patent [19]

Gray

[11] Patent Number: 4,848,438

[45] Date of Patent: * Jul. 18, 1989

[54] METAL SAMPLING

[75] Inventor: Adrian L. Gray, Transvaal Province, South Africa

[73] Assignee: Foseco International Limited, Birmingham, England

[*] Notice: The portion of the term of this patent subsequent to Jun. 13, 2006 has been disclaimed.

[21] Appl. No.: 159,853

[22] Filed: Feb. 24, 1988

Related U.S. Application Data

[63] Continuation-in-part of Ser. No. 158,621, Feb. 22, 1988.

[51] Int. Cl.$^4$ .......................... G01N 1/12; B22D 2/00
[52] U.S. Cl. ..................... 164/4.1; 164/150; 73/864.56; 73/864.59
[58] Field of Search ............... 164/4.1, 150; 73/864.55, 864.56, 864.57, 864.59

[56] References Cited

U.S. PATENT DOCUMENTS

| | | | |
|---|---|---|---|
| 3,221,559 | 12/1965 | Miller, Jr. et al. | 164/4.1 |
| 3,367,189 | 2/1968 | Curry, Jr. | 164/4.1 |
| 3,415,125 | 12/1968 | Collins | 73/864.55 |
| 3,915,014 | 10/1975 | Judge et al. | 73/864.55 |
| 4,069,715 | 1/1978 | Falk | 374/140 |
| 4,093,193 | 6/1978 | Cassidy | 266/87 |

FOREIGN PATENT DOCUMENTS

| | | |
|---|---|---|
| 073746 | 3/1983 | European Pat. Off. . |
| 087219 | 8/1983 | European Pat. Off. . |
| 128665 | 12/1984 | European Pat. Off. . |
| 140512 | 5/1985 | European Pat. Off. . |
| 2254488 | 5/1973 | Fed. Rep. of Germany . |
| 2253211 | 6/1975 | France . |
| 2376403 | 7/1978 | France . |
| 2546625 | 11/1984 | France . |
| 2566904 | 1/1986 | France . |
| 1173849 | 12/1969 | United Kingdom . |
| 1239547 | 7/1971 | United Kingdom . |
| 1274618 | 5/1972 | United Kingdom . |
| 1349774 | 4/1974 | United Kingdom . |
| 1396140 | 6/1975 | United Kingdom . |
| 1488052 | 10/1977 | United Kingdom . |
| 1492268 | 11/1977 | United Kingdom . |
| 2167326A | 5/1986 | United Kingdom . |

Primary Examiner—Richard K. Seidel
Attorney, Agent, or Firm—Nixon & Vanderhye

[57] ABSTRACT

A sampler compries a mould (2) held in a slot (8) at the end of a tube (6) having a cardboard inner wall and an outer protective coating (7), the end of the tube (6) being received in the socket (10) of a body (9), a bore (11) extending between the socket (10) and the outside of the body (9) so that molten metal may reach the mould.

15 Claims, 1 Drawing Sheet

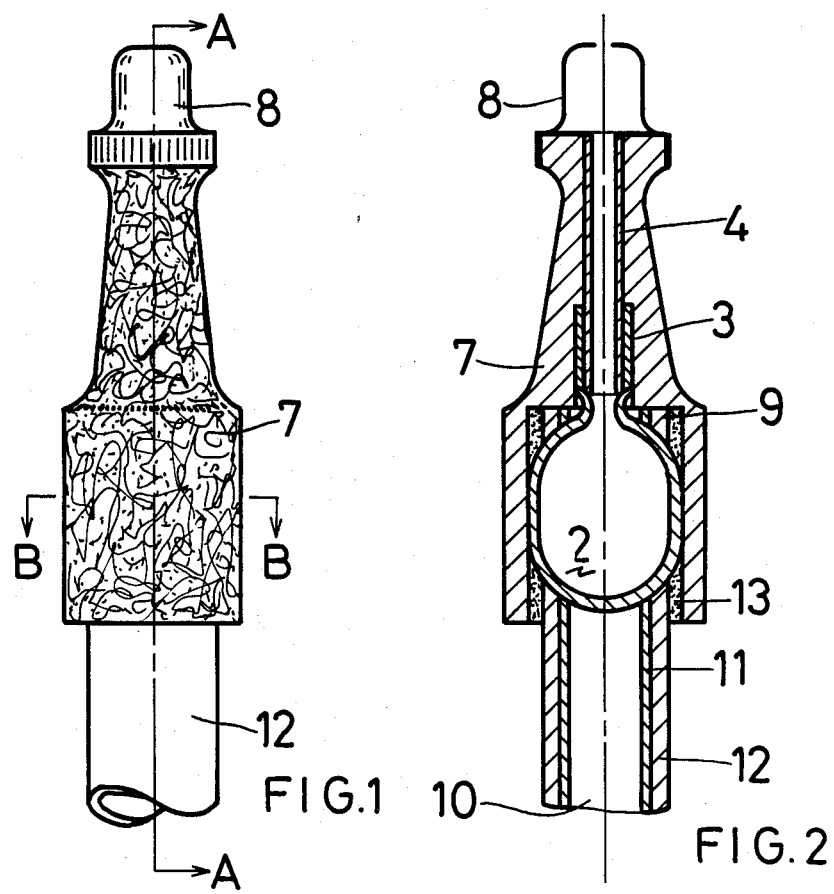
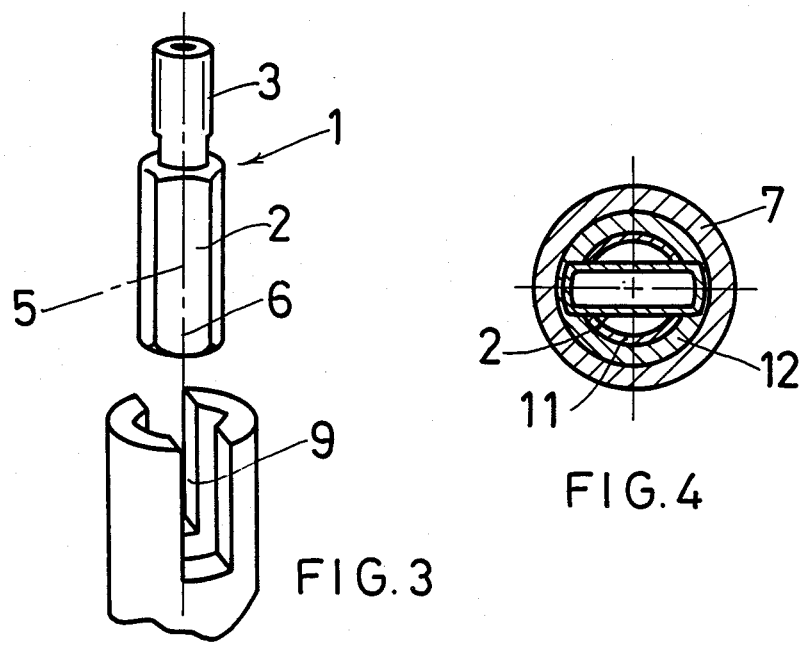

METAL SAMPLING

CROSS-REFERENCE TO RELATED APPLICATION

This application is a continuation-in-part of my application Ser. No. 158,621, filed Feb. 22, 1988, the disclosure of which is hereby incorporated by reference herein.

The invention relates to the sampling of molten metal by immersion of a sampler in a metal melt. Such a sample is obtained by immersing a mould including a glass tube extension into the melt, allowing molten metal into the mould and withdrawing the mould. The metal freezes to form a disc shaped portion and a pin like extension. The disc surface is polished to provide a surface for spectro-graphic analysis. In use, the mould is glued in the end of a thick walled cardboard tube which is held on a steel immersion lance, and a thin metal cap is placed over the inlet end of the glass tube to penetrate the slag layer on top of the melt.

This type of sampler has disadvantages. There is a violent reaction between the cardboard tube and the melt which limits the depth of insertion of the sampler. It can also be difficult to separate the mould containing the sample from the cardboard tube.

The invention is based on the realisation that such difficulties can be avoided if the tube and the mould is provided with a protective coating, preferably one which in use will form a glass or glass-like surface.

According to one aspect of the invention there is provided a sampler comprising a mould to receive a sample of molten metal, the mould being held in the end of a tube of cardboard or like organic material for immersion in the molten metal *characterised in that* the portion of the tube to contact molten metal is provided with a protective coating of refractory composition.

Preferably, the refractory composition includes ingredients which form a protective glass or glass-like surface on contact with the molten metal. Most preferably, sources of sodium oxide, potassium oxide and silica are present in the composition to form a protective glass.

When a tube protected by such a coating is contacted with the molten metal the glass or the ingredients which form glass tend to melt or fuse to form a protective layer which isolate the tube formed of cellulosic material. As a result, little or no violent chemical reaction takes place.

The composition may comprise the glass, refractory fillers and antispalling ingredients. The glass component may comprise up to 75% of the composition which may include up to 5% of potassium or sodium oxide or both and may also include in addition up to 5% of calcium oxide, magnesium oxide or lithium oxide. It is preferred that the composition includes a flux such as fluorspar in a proportion of 1%.

Preferably, the composition comprises as refractory fillers up to 15% of aluminium oxide or zirconium oxide and up to 40% of silicon oxide and as antispalling ingredient up to 15% of low volatile carbonaceous material, e.g. carbon flour, coke, coal or graphite.

The composition may be made into a slurry with water for application to the tube. A slurry viscosity controlling substance and a binder, preferably being a suitable clay and sodium silicate in powder form may be present in a proportion of up to 15% of total solids.

Preferably, the mould is received in the socket of a preformed body made of the refractory composition and the body includes a bore extending between the socket and the outside of the body so that molten metal may enter the bore to reach the mould contained in the socket.

It is preferred that the sample to be provided comprises a disc shape portion and pin portion extending therefrom, and a glass tube for forming the pin extends from the mould into the bore of the body.

In another aspect the invention provides a method of sampling a metal melt *characterised by* inserting a sampler into the melt, allowing the molten metal to enter the mould, removing the sampler and recovering the sample.

Sampling can be easily and effectively achieved because the protective coating prevents a violent reaction when the sampler is immersed into molten metal. The sampler may be easily dipped to great depths and for long periods.

The invention provides a simple assembly which enables conventional sampling to be effected expeditiously and effectively at low cost.

An example of this invention will be described with reference to the accompanying drawings in which:

FIG. 1 is an elevation of the sampler

FIG. 2 is a vertical section through FIG. 1 on line A—A

FIG. 3 is an exploded view of the metal sampling mould and the tube, and

FIG. 4 is a cross-section through FIG. 1 on line B—B.

As shown the sampler comprises a longitudinally split metal mould 1 of conventional form shaped to provide a flat disclike body 2 and a neck portion 3. A glass tube 4 projects from the neck of the mould 2 so that the sample formed will have a classic pin. Venting apertures 5 are present along the joint line of the mould 1.

A thin wall tube of cardboard or like cellulose material 6 and of the size used to hold thermocouples is provided with a relatively thick protective coating of refractory composition 7 including glass or glass forming ingredients. It will be noted that the cardboard wall is relatively thin and the coating is thicker, but need not be so. A slot 8 is formed in the end of the tube to receive the mould. A body 9 is moulded of the same composition. The body has a socket 10 to receive the mould 2 located in the slot 8 of the tube 6. A bore 11 leads from the blind end wall of the socket 10 to the free end of the body. The mould 2 is held in the socket 10 by glue 13. A metal cap 12 is fitted to that free end.

A sampler is made by mounting the mould 2 in the slot 8 of the tube 6 and then filling the mould in the socket 10 of the body 9 with the glass tube 4 extending into the bore 11. The cap 12 is press fitted on. The sampler is then urged into the melt to collect and recover the sample. Gases may escape from the mould 1 directly through the tube 6.

The sample in the mould body 2 and neck 3 can be recovered by shattering the body 9 and end of the tube 6.

Some examples of the composition according to the invention are as follows. The term flour means particles of below 100 micron, and parts are by weight. The mixtures are slurried in water to form a composition which is applied to the tube or used to form the body.

EXAMPLE 1

| | |
|---|---|
| Glass flour | 65.65 |
| Zircon flour | 7.55 |
| Fluorspar | 1.00 |
| Carbon flour | 10.00 |
| Western Province Ball Clay | 7.50 |
| Lithium Carbonate | 0.03 |
| Lime | 0.77 |
| Sodium Silicate | 7.50 |

EXAMPLE 2

| | |
|---|---|
| Glass flour | 58.10 |
| Zircon flour | 15.10 |
| Fluorspar | 1.00 |
| Carbon flour | 10.00 |
| Western Province Ball Clay | 7.50 |
| Lithium Carbonate | 0.03 |
| Lime | 0.77 |
| Sodium Silicate | 7.50 |

EXAMPLE 3

| | |
|---|---|
| Glass flour | 50.50 |
| Zircon flour | 22.70 |
| Fluorspar | 1.00 |
| Carbon flour | 10.00 |
| Western Province Ball Clay | 7.50 |
| Lithium Carbonate | 0.03 |
| Lime | 0.77 |
| Sodium Silicate | 7.50 |

EXAMPLE 4

| | |
|---|---|
| Glass flour | 44.00 |
| Zircon flour | 29.20 |
| Fluorspar | 1.00 |
| Carbon flour | 10.00 |
| Western Province Ball Clay | 7.50 |
| Lithium Carbonate | 0.03 |
| Lime | 0.77 |
| Sodium Silicate | 7.50 |

EXAMPLE 5

| | |
|---|---|
| Glass flour | 31.50 |
| Welding flux (basic) | 41.70 |
| Fluorspar | 1.00 |
| Carbon flour | 10.00 |
| Western Province Ball Clay | 7.50 |
| Lithium Carbonate | 0.03 |
| Lime | 0.77 |
| Sodium Silicate | 7.50 |

EXAMPLE 6

| | |
|---|---|
| Soda ash | 11.70 |
| Zircon flour | 22.70 |
| Fluorspar | 1.00 |
| Carbon flour | 10.00 |
| Western Province Ball Clay | 7.50 |
| Lithium Carbonate | 0.03 |
| Lime | 0.77 |
| Sodium Silicate | 7.50 |
| recycled foundry sand | 38.80 |

EXAMPLE 7

| | |
|---|---|
| Zircon flour | 21.05 |
| Andalusite flour | 10.53 |
| Glass flour | 26.32 |
| Welding flux (basic) | 5.26 |
| Carbon flour | 15.79 |
| Sodium Silicate | 21.05 |

The sodium silicate may be applied either in powdered or liquid form. The powdered form is preferable as this has been found to reduce blistering of the material.

EXAMPLE 8

| | |
|---|---|
| Glass flour | 13.39 |
| Zircon flour | 15.62 |
| Carbon flour | 2.23 |
| Clay | 2.23 |
| Calcite or Lime | 0.45 |
| Flourspar | 1.78 |
| Coarse Silica Sand (approx. grain size 1 mm) | 53.55 |
| Sodium Silicate | 10.71 |
| Methocel (Plastisiser) | 0.04 |

The layer formed of this composition may be applied to a layer of silicate bonded sand over a layer of sealant on the tube.

In another aspect the invention includes a body to be located at the leading end of a sampler *characterised in that* the body is formed of a refractory composition and includes a socket to receive the mould of the sampler and a bore extends between the mould and the outside of the body so that molten metal may reach the mould.

I claim:

1. A sampler comprising a mould (2) to receive a sample of molten metal, the mould being held in the end portion of a tube (6) of cardboard or like organic material for immersion in the molten metal said portion of the tube (6) to contact molten metal being provided with a protective coating (7) of refractory composition, which includes ingredients which form a protective glass or glass-like surface on contact with the molten metal.

2. A sampler according to claim 1 characterised in that sources of sodium oxide, potassium oxide and silica are present in the composition to form a protective glass.

3. A sampler according to claim 1 characterised in that the mould (2) is received in the socket (10) of a preformed body (9) made of the refractory composition and the body includes a bore (11) extending between the socket (10) and the outside of the body so that molten metal may enter the bore (11) to reach the mould (2) contained in the socket (10).

4. A sampler according to claim 3 characterised in that the sample to be provided comprises a disc shape portion and pin portion extending therefrom, and a glass tube (4) for forming the pin extends from the mould (2) into the bore (11) of the body (9).

5. A sampler according to claim 3 characterised in that the preformed body (9) of refractory material is frangible so that it and the tube (6) may be broken for access to the sample in the mould after sampling.

6. A sampler according to claim 1 characterised in that a sealant layer is applied to the tube, an overlying layer of bonded coarse sand is formed and the protective coating is applied over the bonded coarse sand layer.

7. A sampler according to claim 1 characterised in that the composition includes an antispalling ingredient comprising up to 15% of a low volatile carbonaceous material.

8. A sampler according to claim 1 characterised in that the composition includes as refractory fillers up to 15% of aluminium oxide or zirconium oxide and up to 40% of silicon oxide.

9. A sampler comprising a mould to receive a sample of molten metal, the mold being held in the end portion of a tube of cardboard or like organic material for immersion in the molten metal, said portion of the tube to contact the molten metal being provided with a protective coating of refractory composition including sources of sodium oxide, potassium oxide, and silica, so as to form a protective glass upon immersion in the molten metal.

10. A sampler comprising a mould to receive a sample of molten metal, the mold being held in the end portion of a tube of cardboard or like organic material for immersion in the molten metal, said portion of the tube to contact the molten metal being provided with a protective coating of refractory composition, and further comprising a sealant layer applied to the tube, and an overlying layer of bonded coarse sand applied over the sealant layer, said protective coating of refractory composition being applied over the bonded coarse sand layer.

11. A sampler according to claim 10 wherein said refractory composition comprises sources of sodium oxide and potassium oxide, which form a protective glass.

12. A sampler comprising a mould to receive a sample of molten metal, the mold being held in the end portion of a tube of cardboard or like organic material for immersion in the molten metal, said portion of the tube to contact the molten metal being provided with a protective coating of refractory composition, said composition including an antispalling ingredient in an amount greater than 0 and comprising up to 15% of a low volatile carbonaceous material.

13. A sampler according to claim 12 wherein a sealant layer is applied to the tube, and an overlying layer of bonded coarse sand is formed over the sealant layer, and said protective coating of refractory composition is applied over the bonded coarse sand layer.

14. A method of sampling a metal melt utilizing a sampler comprising a mould to receive a sample of molten metal, the mould being held in the end portion of a tube of cardboard or like organic material for immersion in the molten metal, said portion of the tube to contact the molten metal being provided with a protective coating of a refractory composition which includes ingredients which form a protective glass or glass-like surface on contact with the molten metal, said method comprising the steps of:
  inserting the sampler into the melt so that the molten metal causes a protective glass or glass-like surface to form on the sampler upon contact with the molten metal;
  causing the molten metal to enter the mould; and
  removing the sampler from the metal melt and recovering the sample from the mould.

15. A method as recited in claim 14 comprising the further step of, prior to insertion of the sampler into the metal melt, of applying a sealant layer to the tube, applying an overlaying layer of bonded coarse sand over the sealant layer, and then providing the protective coating of refractory composition over the bonded coarse sand layer.

* * * * *